(12) United States Patent
Zhang (10) Patent No.: US 10,251,564 B2
(45) Date of Patent: *Apr. 9, 2019

(54) THERMAL PATIENT SIGNAL ANALYSIS (71) Applicant: Siemens Medical Solutions USA, Inc., Malvern, PA (US)

(72) Inventor: Hongxuan Zhang, Palatine, IL (US)

(73) Assignee: Siemens Healthcare GmbH, Erlangen (DE)

( * ) Notice: Subject to any disclaimer, the term of this patent is extended or adjusted under 35 U.S.C. 154(b) by 24 days.

This patent is subject to a terminal disclaimer.

(21) Appl. No.: 14/674,547

(22) Filed: Mar. 31, 2015

(65) Prior Publication Data

US 2016/0287096 A1    Oct. 6, 2016

(51) Int. Cl.
| | |
|---|---|
| *A61B 5/00* | (2006.01) |
| *A61B 5/01* | (2006.01) |
| *A61N 1/39* | (2006.01) |
| *A61N 1/40* | (2006.01) |
| *A61B 5/029* | (2006.01) |
| *A61M 5/172* | (2006.01) |
| *A61N 1/365* | (2006.01) |
| *A61B 5/0205* | (2006.01) |

(Continued)

(52) U.S. Cl.
CPC .......... *A61B 5/02055* (2013.01); *A61B 5/015* (2013.01); *A61B 5/029* (2013.01); *A61N 1/3655* (2013.01); *A61N 1/3925* (2013.01); *A61N 1/403* (2013.01); *A61B 5/0402* (2013.01); *A61B 5/14551* (2013.01); *A61B 5/6813* (2013.01); *A61B 5/7285* (2013.01); *A61M 5/1723* (2013.01); *A61M 2230/005* (2013.01); *A61M 2230/04* (2013.01)

(58) Field of Classification Search
CPC ........ A61M 2230/005; A61M 2230/04; A61M 5/1723; A61N 1/3655; A61N 1/3962; A61B 5/02055; A61B 5/029; A61B 5/0402–5/0472; A61B 5/14551; A61B 5/7278; A61B 5/02–5/0295
USPC ................... 73/202.5, 204.11; 374/100–108; 600/300–301, 407–408, 412, 473–475, 600/481, 483, 508, 526–527
See application file for complete search history.

(56) References Cited

U.S. PATENT DOCUMENTS

| | | |
|---|---|---|
| 4,834,107 A | 5/1989 | Warner et al. |
| 5,025,795 A | 6/1991 | Kunig |

(Continued)

OTHER PUBLICATIONS

Sun et al. The cardiac output from blood pressure algorithms trial, Crit Care Med. Jan. 2009; 37(1): 72-80. doi:10.1097/CCM.0b013e3181930174.*

(Continued)

*Primary Examiner* — Boniface Nganga
*Assistant Examiner* — Jonathan Kuo (57) ABSTRACT

Disclosed herein is a framework for facilitating thermal patient signal analysis. In accordance with one aspect, the framework receives patient signal data including thermal signal data. The framework then segments a region of interest from the thermal signal data. One or more cardiac output indices may be determined based on one or more parameters extracted from the segmented region of interest to characterize cardiac output or stroke volume. A report may then be generated based at least in part on the one or more cardiac output indices.

25 Claims, 7 Drawing Sheets

(51) Int. Cl.
*A61B 5/0402* (2006.01)
*A61B 5/1455* (2006.01)

(56) References Cited

U.S. PATENT DOCUMENTS

| | | | |
|---|---|---|---|
| 5,265,615 A * | 11/1993 | Frank | A61B 5/029 |
| | | | 600/485 |
| 5,509,424 A * | 4/1996 | Al-Ali | A61B 5/028 |
| | | | 128/925 |
| 5,797,395 A | 8/1998 | Martin | |
| 6,004,274 A | 12/1999 | Nolan et al. | |
| 6,162,180 A | 12/2000 | Miesel et al. | |
| 6,186,955 B1 | 2/2001 | Baura | |
| 6,322,514 B1 | 11/2001 | Holte | |
| 6,582,656 B1 | 6/2003 | Steuer et al. | |
| 6,615,064 B1 | 9/2003 | Aldrich | |
| 6,650,940 B1 | 11/2003 | Zhu et al. | |
| 6,681,128 B2 | 1/2004 | Steuer et al. | |
| 6,731,963 B2 | 5/2004 | Finarov et al. | |
| 6,757,554 B2 | 6/2004 | Rubinstein et al. | |
| 6,829,501 B2 | 12/2004 | Nielsen et al. | |
| 7,011,631 B2 | 3/2006 | Davis et al. | |
| 7,024,244 B2 | 4/2006 | Muhlenberg et al. | |
| 7,220,230 B2 | 5/2007 | Roteliuk et al. | |
| 7,422,562 B2 | 9/2008 | Hatib et al. | |
| 7,485,094 B2 | 2/2009 | Marks et al. | |
| 7,904,141 B2 | 3/2011 | Osypka et al. | |
| 7,925,347 B1 | 4/2011 | Bornzin et al. | |
| 7,935,062 B2 | 5/2011 | Karamanoglu et al. | |
| 8,200,308 B2 | 6/2012 | Zhang et al. | |
| 8,465,435 B2 | 6/2013 | Van Goudoever et al. | |
| 8,679,025 B2 | 3/2014 | Harpas et al. | |
| 8,721,556 B2 | 5/2014 | Roteliuk | |
| 8,771,197 B2 | 7/2014 | Hatib et al. | |
| 8,801,618 B2 | 8/2014 | Hatib et al. | |
| 2008/0045847 A1 * | 2/2008 | Farag | A61B 5/02055 |
| | | | 600/500 |
| 2012/0179382 A1 * | 7/2012 | Zhang | A61B 5/02416 |
| | | | 702/19 |
| 2013/0218038 A1 * | 8/2013 | Zhang | A61B 5/02055 |
| | | | 600/526 |
| 2015/0018632 A1 * | 1/2015 | Khair | A61B 5/026 |
| | | | 600/301 |

OTHER PUBLICATIONS

Zhang and Fan, Computation Biomechanics of the Musculoskeletal System, Sep. 11, 2014, CRC Press, 1st edition, p. 312, ISBN 1466588039.*

Kuo, Yu, Meng, Micromachined Thermal Flow Sensors, Jul. 23, 2012, Micromachines 2012, 3, 550-573, doi: 10.3390/mi3030550.*

* cited by examiner

Fig. 7 ial signals.

THERMAL PATIENT SIGNAL ANALYSIS

TECHNICAL FIELD

The present disclosure generally relates to systems and methods for analyzing thermal patient signals.

BACKGROUND

The cardiovascular system has five main components: (1) a pump (i.e., heart); (2) a carrier fluid (i.e., blood); (3) a distribution system (i.e., arteries); (4) an exchange system (i.e., capillary network); and (5) a collection system (i.e., veins). Blood pressure is the driving force that propels blood through the distribution network. Stroke volume (SV) is the volume of blood pumped by the right or left ventricle of the heart in one contraction. Specifically, it is the volume of blood ejected from one of the ventricles during systole. The stroke volume is not all of the blood contained in the ventricle. Normally, only about two-thirds of the blood in the ventricle is ejected with each beat. The volume of blood that is actually pumped from the ventricle is the stroke volume (SV).

Cardiac output (CO) is determined by stroke volume (SV) and heart rate (HR) as follows:

$$CO = HR \times SV \quad (1)$$

Typically, ventricular stroke volume (SV) is the difference between the ventricular end-diastolic volume (EDV) and the end-systolic volume (ESV).

$$SV = EDV - ESV \quad (2)$$

The EDV is the filled volume of the ventricle prior to contraction, and the ESV is the residual volume of blood remaining in the ventricle after ejection. In a typical heart, the EDV is about 120 ml of blood and the ESV about 50 ml of blood. The difference in these two volumes, 70 ml, represents the SV. Therefore, any factor that alters either the EDV or the ESV will change SV.

CO/SV measurement may provide a useful approach for characterizing cardiac pathology and predicting life-threatening events. Currently, there are three methods for CO and SV measurement and cardiac health status index calculation: (1) Fick method; (2) thermodilution method; and (3) angiographic image method. The Fick method is an invasive method that needs at least two blood samples and requires knowledge of oxygen consumption or VO2. Thermodilution is another invasive method that involves the injection of saline into the central venous pressure CVP/right atrial (RA) port. The saline flows through the right ventricle (RV) and cools the thermistor in the pulmonary artery (PA), at which the rate and degree can be utilized for CO and SV calculation. Angiographic method can also be utilized for CO and SV calculation, by estimating cardiac image volume at EoD (end of diastolic) and EoS (end of systolic) times. Such method usually requires extensive clinical experience and generates estimations with tremendous deviations.

These approaches have several shortcomings, such as requiring blood samples in the Fick cardiac output measurement, subjective and inaccurate cardiac output calculation based on images of EoD and EoS points in angiographic images, analysis deviation of measuring data and calculation in thermodilution-based cardiac output monitoring, etc. Further, current CO and SV calculation methods are based on complicated clinical devices and systems, such as invasive blood pressure catheters, X-ray image system, etc., which may increase patient risk due to tissue damage, radioactivity dose, complicated medical procedure, timing, sensitivity, false alarm, etc.

Most known CO/SV analyses are not accurate, since the corresponding data acquisition is not precise. For example, blood pressure measured in a noisy environment does not yield accurate data. Current image-based CO and SV calculations, such as those based on fluoroscopic and ultrasound images, calculate volume by measuring the size of the heart captured in the images in two or three dimensions. Such measurements are typically not accurate, especially for EoD and EoS stages, due to imprecise timing or gating. Current thermodilution methods typically use an injection waveform, which is invasive. So far, there are no known efficient quantitative and qualitative non-invasive clinical approaches for estimating CO and SV with good accuracy, sensitivity and stability.

Known less-invasive or non-invasive methods for estimating SV utilize blood stroke volume within local vessels to proportionally estimate the heart SV. The non-linear relationship between measured and actual heart SVs may result in huge calculation errors and subsequent false alarms, especially in critical care monitoring. There are no known accurate non-linear methods to bridge the local calculation index and true heart cardiac output.

Known methods for CO calculation do not fully or efficiently use vital sign signals (e.g., blood pressure), which are closely related to hemodynamic signals. Recently, some studies have been made on least invasive sensing of blood pressure to estimate CO. However, such methods also rely on catheter technologies, which limit the clinical applications. In addition, known clinical methods for CO/SV estimation require extensive clinical experience and knowledge to, for example, interpret parameters and evaluate calculation accuracy. This may impose some limitations for certain medical users. Some cardiac output determination methods rely on the quality of the sensor and acquired signals. Noisy environment or noisy data acquisition may cause false calculations and unreliable cardiac function estimation. Such noise may come from the power line, patient movement, or patient treatment process, such as pacing and drug delivery.

SUMMARY

The present disclosure relates to a framework for facilitating thermal patient signal analysis. In accordance with one aspect, the framework receives patient signal data including thermal signal data. The framework then segments a region of interest from the thermal signal data. One or more cardiac output indices may be determined based on one or more parameters extracted from the segmented region of interest to characterize cardiac output or stroke volume. A report may then be generated based at least in part on the one or more cardiac output indices.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

DETAILED DESCRIPTION

In the following description, numerous specific details are set forth such as examples of specific components, devices, methods, etc., in order to provide a thorough understanding of embodiments of the present disclosure. It will be apparent, however, to one skilled in the art that these specific details need not be employed to practice embodiments of the present disclosure. In other instances, well-known materials or methods have not been described in detail in order to avoid unnecessarily obscuring embodiments of the present disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

It is to be understood that the system and methods described herein may be implemented in various forms of hardware, software, firmware, special purpose processors, or a combination thereof. Preferably, the present disclosure is implemented in software as an application (e.g., n-tier application) comprising program instructions that are tangibly embodied on one or more program storage devices (e.g., magnetic floppy disk, RAM, CD ROM, ROM, etc.), and executable by any device or machine comprising suitable architecture. If written in a programming language conforming to a recognized standard, sequences of instructions designed to implement the methods can be compiled for execution on a variety of hardware platforms and for interface to a variety of operating systems. In addition, embodiments of the present framework are not described with reference to any particular programming language. It will be appreciated that a variety of programming languages may be used to implement embodiments of the present disclosure.

The present framework provides a link between cardiac output (CO) and blood flow in small blood vessels (or capillaries). Blood flow in any artery branches of the human body may be measured by temperature or heat pattern. More particularly, the present framework builds a bridge between non-invasive blood temperature (or thermal) signals in circulation arteries (e.g., blood heat monitoring on wrist, fingertip, forehead, etc.) and cardiac output (or stroke volume) pumped from the heart chambers (e.g., left ventricle).

One aspect of the present framework characterizes cardiac output (or stroke volume) by analyzing non-invasive blood circulation thermal (or temperature) waveform signals. A thermal (or heat or temperature) sensor system may be provided for non-invasive signal data acquisition. The non-invasive blood thermal measurements and data calculation may be utilized to qualitatively and quantitatively capture heart function and blood flow characteristics. By using linear and/or nonlinear calculation models based on blood flow thermal mode and pattern (e.g., thermal energy, thermal variability, variation, etc.), cardiac output may be accurately derived with better sensitivity and stability, especially in noisy conditions. The present framework may also provide a new approach for cardiac tissues and functions monitoring, diagnosis and evaluation, such as identifying cardiac disorders, differentiating cardiac arrhythmias, characterizing pathological severities, predicting life-threatening events, and even evaluating drug delivery and effects. These and other exemplary features and advantages will be described in the following.

In the following description, the terms "stroke volume" and "cardiac output" are used interchangeably in the context of the present framework. It should also be appreciated that the terms "temperature", "heat" and "thermal" may also be used interchangeably in the context of the present framework.

Figure 1:
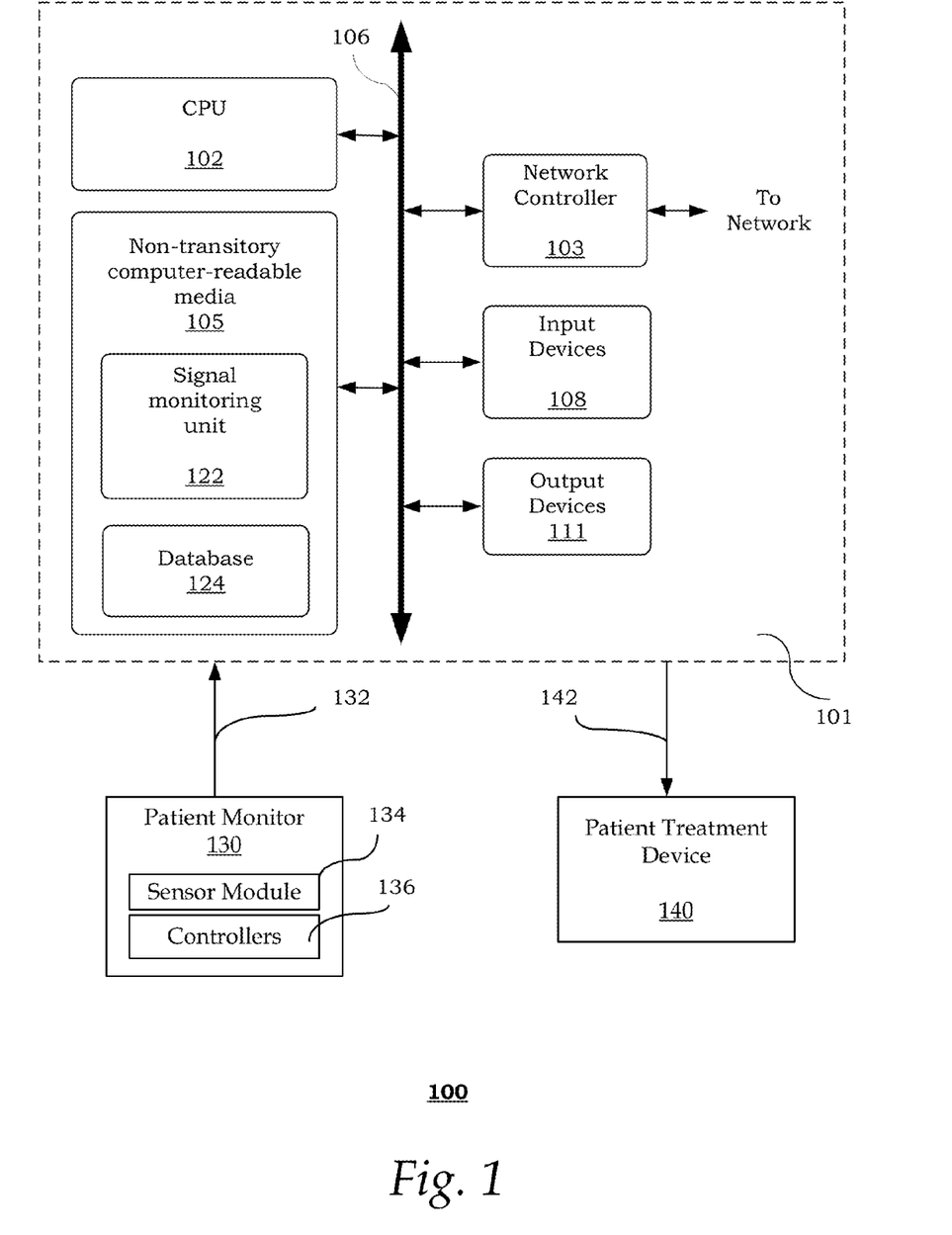
FIG. 1 shows an exemplary system.

FIG. 1 shows an exemplary system 100 for implementing a method and system of the present disclosure. It is to be understood that, because some of the constituent system components and method steps depicted in the accompanying figures can be implemented in software, the actual connections between the system components (or the method steps) may differ depending upon the manner in which the present framework is programmed. For example, the system 100 may be implemented in a client-server, peer-to-peer (P2P) or master/slave configuration. In such configurations, the system 100 may be communicatively coupled to other systems or components via a network, such as an Intranet, a local area network (LAN), a wide area network (WAN), a P2P network, a global computer network (e.g., Internet), a wireless communication network, or any combination thereof. Given the teachings of the present disclosure provided herein, one of ordinary skill in the related art will be able to contemplate these and similar implementations or configurations of the present disclosure.

As shown in FIG. 1, the system 100 may include a computer system 101, a patient monitor 130 and a patient treatment device 140. The computer system 101 may include, inter alia, a central processing unit (CPU) or processor device 102, a non-transitory computer-readable media 105, one or more output devices 111 (e.g., printer, display monitor, projector, speaker, etc.), a network controller 103, an internal bus 106 and one or more input devices 108 such as, for example, a keyboard, mouse, touch screen, gesture and/or voice recognition module, etc. Computer system 101 may further include support circuits such as a cache, a power supply, clock circuits and a communication bus. Various other peripheral devices, such as additional data storage devices and printing devices, may also be connected to the computer system 101.

The present technology may be implemented in various forms of hardware, software, firmware, special purpose processors, or a combination thereof, either as part of a microinstruction code or as part of an application program or software product, or a combination thereof, which is executed via the operating system. In one implementation, the techniques described herein are as computer-readable program code tangibly embodied in non-transitory computer-readable media 105. Non-transitory computer-readable media or memory device 105 may include random access memory (RAM), read only memory (ROM), magnetic floppy disk, flash memory, and other types of memories, or a combination thereof. The present techniques may be implemented by signal monitoring unit 122 that is stored in computer-readable media 105. As such, the computer system 101 is a general-purpose computer system that becomes a specific-purpose computer system when executing the computer-readable program code.

The same or different computer-readable media 105 may be used for storing a database 124. Database 124 may include a repository of determined parameters, indices and/or ratios, selectable predetermined functions, patient signal data (e.g., temperature, heat, thermal, non-invasive blood pressure (NIBP) signal data, oximetric (SPO2) signal data, electrophysiological signal data such as electrocardiograms (ECG), intra-cardiac electrograms (ICEG), respiration signal data, hemodynamic or vital sign data, etc.), patient data (e.g., demographic data, pathology history, etc.), other input data and/or other derived output parameters.

One or more components of system 100 (e.g., computer system 101 and patient monitor 130) may be implemented in a critical care, medical recording or monitoring device, which may be a stationary (e.g., bedside), mobile or portable system, or implemented on the patient's body. In some implementations, computer system 101 filters and/or converts patient signal data measured or acquired by patient monitor 130. Exemplary types of patient signal data include, but are not limited to, non-invasive temperature signal, temperature variation signal, heat (or thermal) signal, ECG signal, NIBP signal, SPO2 signal, and so forth. System 101 may further condition, filter and/or convert temperature and thermal signals, and transmit such signals to other systems. Further, system 101 may determine and display cardiac output (CO) or stroke volume (SV) and other associated parameters, ratios, indices and/or diagnoses (e.g., health status) based on the patient signal data. System 101 may be further used to capture all disease-related patient signal distortions and predict life-threatening events. In some implementations, temperature and heat-based calculations may be performed to diagnose CO malfunctions, which can help to determine cardiac arrhythmia and other pathologies. It should be appreciated that one or more functions of computer system 101 may also be performed by patient monitor 130.

As shown in FIG. 1, system 101 may be communicatively coupled to patient monitor 130 via communication channel 132 (e.g., wireless or wired) to receive patient signal data. Patient monitor 130 may include a sensor module 134 and controllers 136. Patient monitor 130 may further include an indicator, internal power supply (e.g., battery) or an interface device to receive power from an external power supply (e.g., wired interface or wireless power-voltage converter), as well as other components (e.g., display, memory, etc.).

Sensor module 134 may include one or more different kinds of thermal sensors with different size, resolution, etc. Thermal sensors may also be herein referred to as temperature or heat sensors. Thermal sensors may be contact or non-contact sensors. Different sensors and/or probes may be utilized for different positions and clinical applications. Sensor module 134 may include, for example, an infrared heat-sensitive sensor, temperature-sensitive impedance sensor, chemical action temperature-sensitive heat sensor, semiconductor temperature-sensitive sensor, etc. In some implementations, high resolution and sensitivity sensors and/or probes are used to capture thermal modes (or patterns) for the main working temperature range (e.g., 30 to 50 degrees) of human body temperature. Other data ranges may also be used. Sensor module 134 may further include non-thermal sensors, such as an electrocardiogram sensor, a non-invasive blood pressure sensor or an oximetric (e.g., SPO2) sensor, to acquire other types vital signs and/or hemodynamic signals.

System 101 may further be communicatively coupled to patient treatment device 140 via communication channel 142 (e.g., wireless or wired) to provide closed loop treatment in response to determined parameters, ratios and/or indices. Patient treatment device 140 may include, but is not limited to, an intravenous (IV) device, pacing device, implantable cardiac defibrillator (ICD) system or other implantable device, hyperthermia device, and so forth. System 101 may serve to generate control parameters (e.g., IV control, pacing-stim control, energy duration pacing site, drug delivery speed, ICD parameter control, hyperthermia control, etc.) to control the patient treatment device 140 in response to determined parameters, ratios and/or indices (e.g., CO indices).

Figure 2:
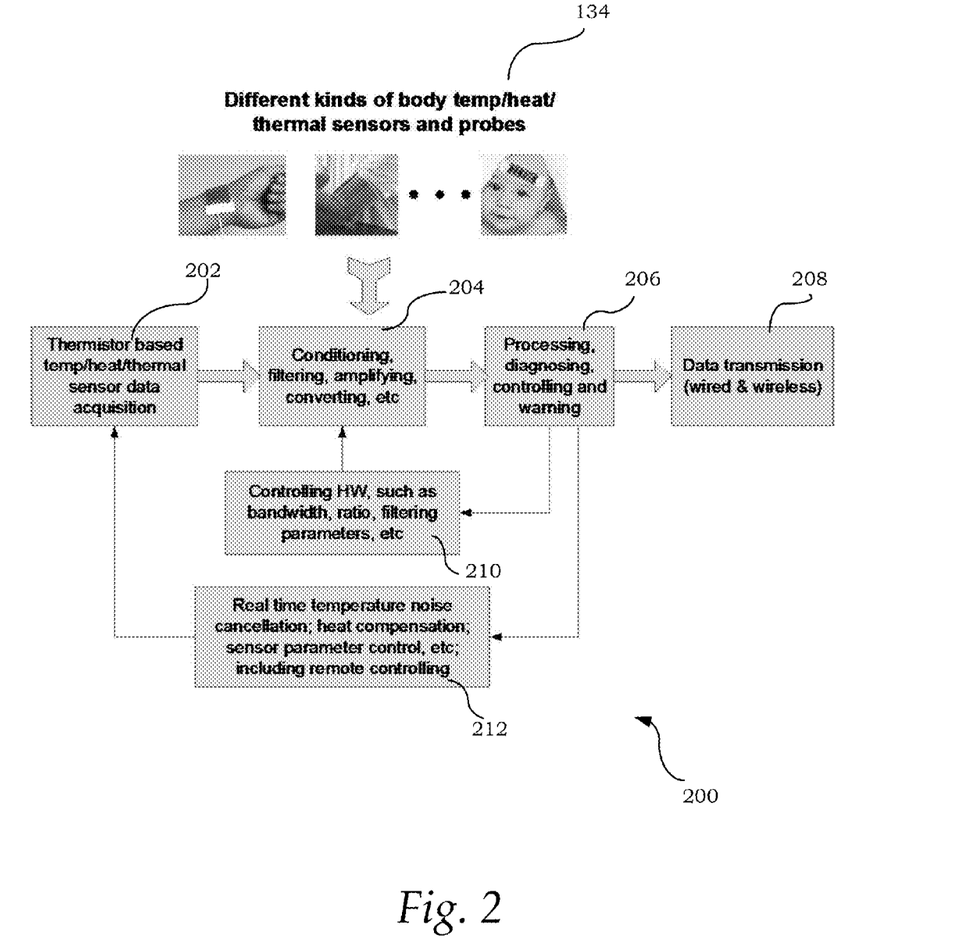
FIG. 2 illustrates an exemplary closed-loop adaptive control method.

FIG. 2 illustrates an exemplary closed-loop adaptive control method 200 that processes thermal signal data from a thermal sensor module 134. Hardware parameter control, temperature noise cancellation and heat compensation may be achieved in real time by patient monitor 130 or remotely by system 101 via wired or wireless communication and command control. Thermal sensor module 134 may include different kinds of patient signal sensors for simultaneously recording thermal signals with different types of vital signs and/or hemodynamic signals (e.g., ECG, SPO2, NIBP, etc.) to further facilitate segmentation, categorization and characterization of thermal signal data.

In some implementations, patient monitor 130 includes a thermal sensor module 134 (e.g., contact sensors, thermistors, etc.) and four controllers 136: (1) pre-processing controller or front electronics for pre-processing (e.g., conditioning, filtering, converting, etc.) thermal signals; (2) central controller which may include a data transmission module for facilitating communications of data, commands, power, etc., via wired or wireless channels; (3) feedback controller for adjusting bandwidth, coefficients, etc., used in signal conditioning and filtering in real time; (4) noise controller for adaptive closed-loop thermal noise cancellation in real time. The noise may arise from, for example, environmental noise, drug delivery, treatment procedure, such as hyperthermia, etc.

In some implementations, thermal sensor module 134 includes a high resolution thermistor used for tracking, capturing, converting, recording and diagnosing thermal pattern changes, which can help to characterize cardiac functions, such as cardiac output, cardiac arrhythmia and pathological events, etc. Thermal sensor module 134 may include different kinds of thermistors for various temperature sensitive ranges, thermal noise levels, heat converting accuracies, etc. Such thermistors may be adaptively and automatically adjusted. Thermal sensor module 134 may be configured to be removably attached to different positions on the patient's body (e.g., wrist, arm, forehead, etc.). In addition, thermal sensor module 134 may be disposable or reusable.

As shown by the exemplary method 200 illustrated in FIG. 2, at 202, thermal sensor module 134 may first be used to acquire thermal (or heat or temperature) signal data. At 204, pre-processing controller may then perform conditioning, filtering, amplification, conversion, etc., of the thermal signal data. At 206, central controller may process the pre-processed signal data and determine diagnosis, control parameters, warning parameters, etc. At 208, data transmission module may perform data transmission via, for example, a wired or wireless communications channel. At 210, feedback controller may perform various types of HW control, such as adjusting bandwidth, ratio, filtering parameters, etc., based on the processed results from the central controller. At 212, noise controller may perform real-time temperature noise cancellation, heat compensation, sensor control parameters adjustment, etc., based on processed results from the central controller.

Figure 3:
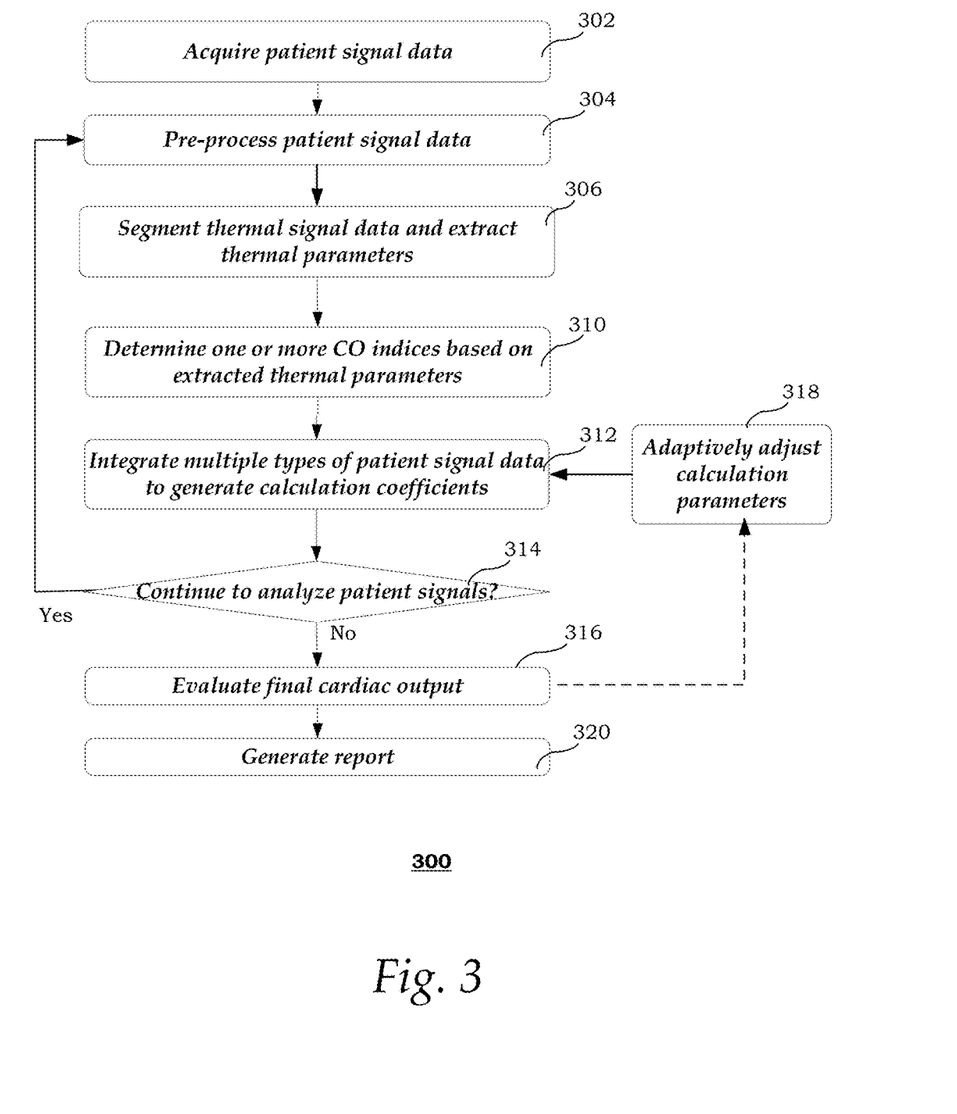
FIG. 3 shows an exemplary method of analyzing patient signal data.

FIG. 3 shows an exemplary method 300 of analyzing patient signal data. The steps of the method 300 may be performed in the order shown or a different order. Additional, different, or fewer steps may be provided. Further, the method 300 may be implemented with the system 100 of FIG. 1, a different system, or a combination thereof.

At 302, patient signal data is acquired. Such patient signal data may be represented by a waveform or graph with, for example, time represented on the x-axis and voltage or amplitude represented on the y-axis. Such patient signal data includes thermal signal data that is non-invasively acquired from a surface of a patient's body. Thermal signal data may include any type of signal data that is generated in response to heat from blood flowing in the blood vessels. Such thermal signal data may include, for example, temperature signals, temperature speed signals, temperature acceleration signals, thermal pulse, heat pulse, temperature variation pulse waveforms from different locations of the body (e.g., wrist, arm, leg, forehead, etc.), and so forth. Such thermal signal data may be acquired by, for example, sensor module 134, as previously described with reference to FIGS. 1 and 2.

In some implementations, the patient signal data includes cardiac electrophysiological signal data, such as electrocardiogram (ECG) data, surface ECG data, etc. Alternatively, or additionally, other types of electrophysiological signal data, such as hemodynamic (HEMO) signal data (e.g., invasive blood pressure (IBP) signal data, non-invasive blood pressure signal data, cardiac output signals, etc.), respiration (or capnographic) signal data, blood pressure data, oximetric (SPO2) signal data, capnographic signal data, temperature, and/or other vital sign signal data, other measurable patient biometric, physiological or medical signals, may also be acquired. In addition, other patient information, such as demographic data, clinical application and patient status, including, but not limited to, weight, height, gender, age, allergies, medications, pathology history, pathology treatment history, etc., may also be acquired.

Figure 4:
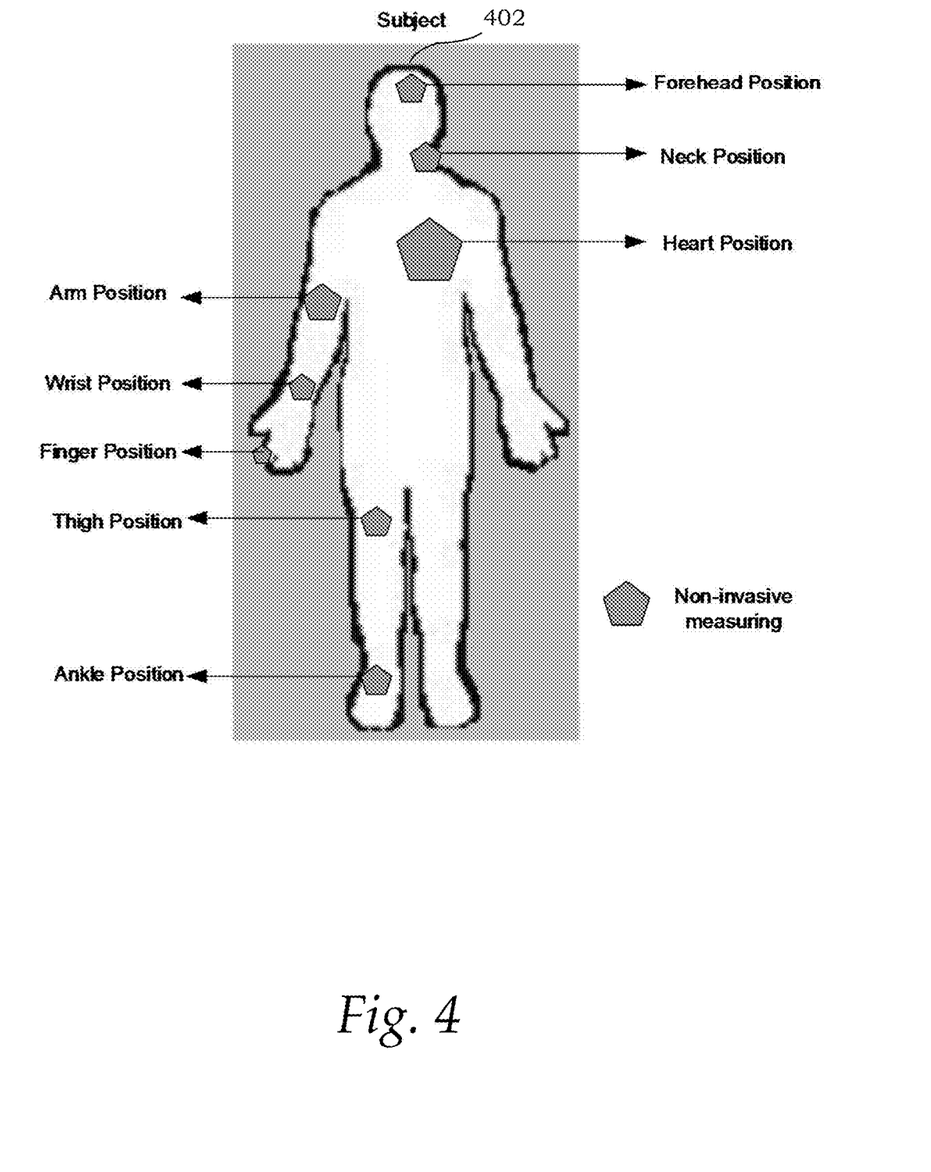
FIG. 4 shows various exemplary positions on a subject's body that may be used to non-invasively acquire patient signal data.

Thermal signal data and/or other types of patient signal data may be acquired from different parts of the body. FIG. 4 shows various exemplary positions on a subject's body 402 that may be used to non-invasively acquire patient signal data. As shown, the different positions may include, but are not limited to, the forehead, neck, heart position, arm, wrist, finger (capillary system), thigh, ankle, and so forth. According to the different positions, different kinds of thermal sensors and heat converters may be utilized. For example, for the wrist position, a thermistor and high resolution thermocouple may be used for recoding heat and temperature mode data, such as temperature variations and instant heat changing speeds.

Returning to FIG. 3, at 304, the patient signal data is pre-processed. As discussed previously, system 101 or pre-processing controller may perform the pre-processing by conditioning, filtering, converting, amplifying, digitizing, buffering, etc., patient signal data acquired by sensor module 134. For example, the patient signal data may be pre-filtered and amplified for display on, for instance, computer system 101. The patient signal data may be filtered to remove unwanted patient movement and respiratory artifacts, as well as power line noise. The filter may be adaptively selected in response to data indicating clinical application (e.g. ischemia detection application, rhythm analysis application). The patient signal data may be conditioned, converted, amplified, buffered, filtered and/or digitized to produce a continuous stream of digitized samples.

At 306, patient signal monitoring unit 122 segments the waveform of the thermal signal data and extracts one or more thermal parameters from the segmented waveform. The thermal parameters may be extracted from a region of interest (ROI), which is any portion of the waveform that is identified for further analysis. The region of interest may include, for example, one or more thermal cycles. The region of interest may be selected based on the occurrence of one or more key points (e.g., peak or maximum point) in another patient signal (e.g., ECG).

Figure 5:
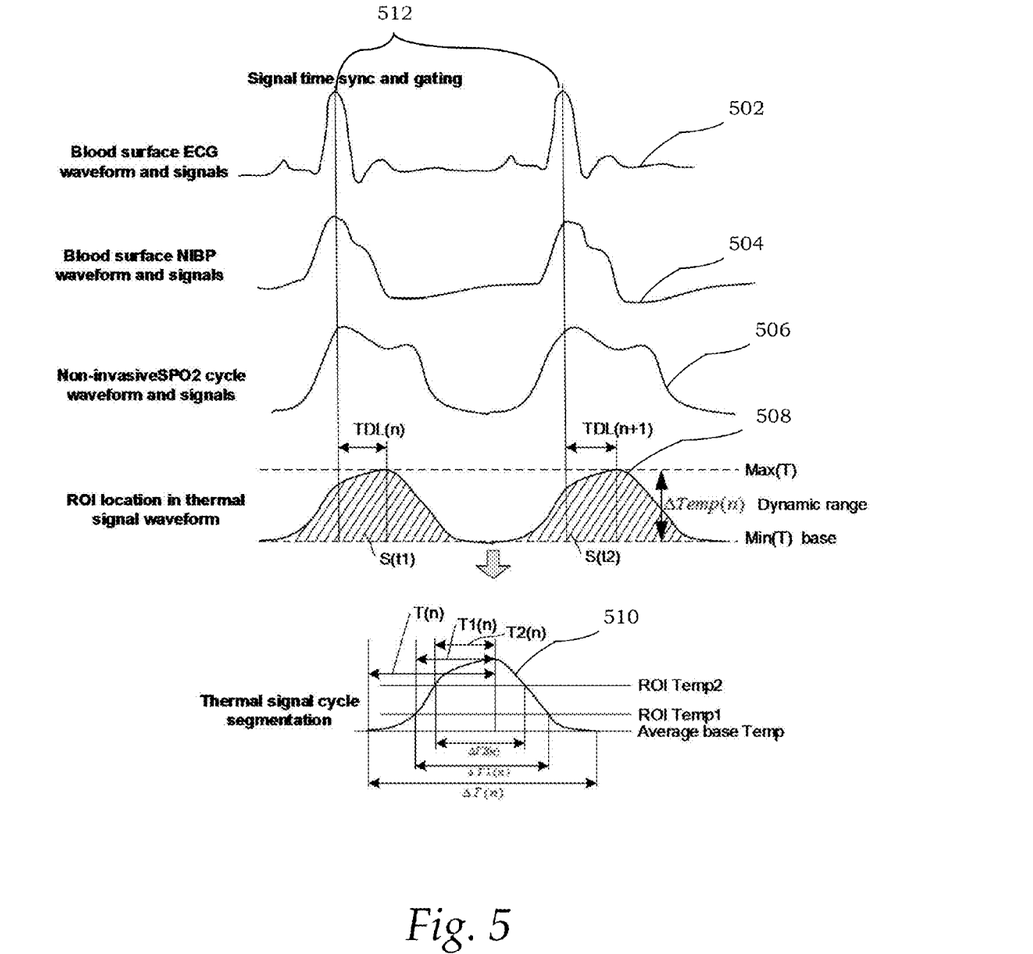
FIG. 5 shows multiple types of exemplary patient signal waveforms and an exemplary segmentation of the thermal signal cycle waveform.

As discussed previously, multiple kinds of non-thermal patient signals (e.g., body surface ECG, SPO2, etc.) may be simultaneously recorded and converted together with thermal signal data. FIG. 5 shows multiple types of exemplary patient signal waveforms (502, 504, 506, 508) and an exemplary segmentation of the thermal signal cycle waveform 510. More particularly, the patient signal waveforms may include an ECG signal waveform 502, an NIBP signal waveform 504, a non-invasive oximetric (SPO2) signal waveform 506 and a temperature (or thermal) signal waveform 508. Such patient signal data may be simultaneously acquired by, for example, the sensor module 134 from the same position on a patient's body. Different patient signals may be used for gating and synchronizing the temperature signal waveform 508. For example, as shown in FIG. 5, the temperature signal 508 is synchronized with R wave peaks 512 of the ECG signal waveform 502. The region of interest may be extracted from the temperature signal waveform 508 based on the occurrence of one or more R wave peaks 512.

In some implementations, a cycle 510 of the temperature signal waveform 508 is segmented into different ROI portions. Parameters may be extracted from the segmented waveform for use in determining indices that characterize CO (or SV). Such parameters may include, for example, time durations, time lengths, waveform areas (S(t1), S(t2), etc.), temperature amplitude, temperature dynamic amplitude range, etc.

Referring back to FIG. 3, at 310, patient signal monitoring unit 122 determines one or more cardiac output (CO) indices based on the extracted thermal parameters. Based on clinical application requirements and environmental factors (e.g., noise), different kinds of indices may be used to characterize CO. In some implementations, the CO indices include an amplitude index, an amplitude range index, a waveform area index, a time-based index, a delay timing index, a variation index and a dynamic change index. Other types of CO indices are also useful. In the following description, reference may be made to the parameters extracted from segmented thermal signal cycle 510 as illustrated in FIG. 5.

Amplitude CO indices may be determined based on temperature amplitude parameters, as follows:

$$CO_{T\_Amp1}(n) = \alpha_1(t) \cdot (\text{Max}(n) - \text{Min}(n)) \quad (3)$$

$$CO_{T\_Amp2}(n) = \alpha_2(t) \cdot \text{Average}(A(n), \text{cycle}(n)) \quad (4)$$

wherein $CO_{T\_Amp1}(n)$ and $CO_{T\_Amp2}(n)$ are first and second amplitude CO indices; Max(n) and Min(n) are maximum and minimum amplitude values of the $n^{th}$ thermal signal cycle; Average(A(n), cycle(n)) is the average amplitude value for the $n^{th}$ thermal signal cycle; $\alpha_1(t)$ and $\alpha_2(t)$ are calculation coefficients or ratios between the temperature amplitude parameter sand CO indices, which are usually dynamic for different patients and can be adaptively updated by a coefficient estimation module. For a specific patient and a stable situation, $\alpha_1$ (t) and $\alpha_2$ (t) are usually stable and treated as constant factors.

An amplitude range CO index may be determined based on at least one temperature amplitude statistical parameter as follows:

$$CO_{T\_Amp\_var}(n) = \beta(t) \cdot \frac{\text{Average}(A(n), \text{cycle}(n))}{\mu(A(n), \text{cycle}(n))} \quad (5)$$

wherein $CO_{T\_Amp\_var}(n)$ is the amplitude range CO index; Average(A(n), cycle(n)) is the average amplitude value for the $n^{th}$ thermal signal cycle; $\mu(A(n), \text{cycle}(n))$ is the standard deviation value of the amplitude for the $n^{th}$ thermal signal cycle; $\beta(t)$ is the calculation coefficient or ratio between the temperature amplitude variation parameter and CO index. $\beta(t)$ is usually dynamic for different patients and can be adaptively updated by a coefficient estimation module. For a specific patient and a stable situation, $\beta(t)$ is usually stable and treated as a constant factor. In equation (5), first order statistical variation of the temperature amplitude is utilized for CO index determination. However, it should be appreciated that higher order statistical parameters may also be used for CO estimation to achieve higher accuracy and stability.

Waveform area CO indices may be determined based on temperature waveform area, as follows:

$$CO_{T\_area1}(n) = \lambda(t) \cdot \int_{t \in S(n)} |A(t)| \quad (6)$$

$$CO_{T\_area2}(n) = \lambda(t) \cdot \int_{t \in S(n)} |A(t)|^2 \quad (7)$$

wherein $CO_{T\_area1}(n)$ and $CO_{T\_area2}(n)$ are first and second waveform area CO indices; A(t) is a thermal signal waveform amplitude value at timing t; S(n) denotes a whole time length of the $n^{th}$ thermal signal cycle;

$$\int_{t \in S(n)} |A(t)| \text{ and } \int_{t \in S(n)} |A(t)|^2$$

are integrals of the thermal signal waveform covering area size |A(t)| and energy $|A(t)|^2$; $\lambda(t)$ is a calculation coefficient or ratio between the temperature area or volume parameter and CO index. $\lambda(t)$ is usually dynamic for different patients and can be adaptively updated by a coefficient estimation module. For a specific patient and a stable situation, $\lambda(t)$ is usually stable and treated as a constant factor.

Time-based CO indices may be determined based on temperature ROI time lengths or durations as follows:

$$CO_{T\_dur\_0}(n) = \gamma_0(t) \cdot \Delta T(n) \quad (8)$$

$$CO_{T\_dur\_1}(n) = \gamma_1(t) \cdot \Delta T1(n) \quad (9)$$

$$CO_{T\_dur\_2}(n) = \gamma_2(t) \cdot \Delta T2(n) \quad (10)$$

$$CO_{T\_time\_0}(n) = \omega_0(t) \cdot T(n) \quad (11)$$

$$CO_{T\_time\_1}(n) = \omega_1(t) \cdot T1(n) \quad (12)$$

$$CO_{T\_time\_2}(n) = \omega_2(t) \cdot T2(n) \quad (13)$$

wherein $CO_{T\_dur\_x}(n)$ and $CO_{T\_time\_x}(n)$ denote time-based CO indices that are calculated based on time length and time duration of ROI portions from the nth thermal signal cycle; $\gamma_x(t)$ and $\omega_x(t)$ are coefficients or ratios between temperature ROI time length or duration and the CO index; $\Delta Tx(n)$ denotes the time duration of the ROI signal portion in the segmented $n^{th}$ thermal signal cycle; Tx(n) represents the time length of the ROI signal portion in the segmented $n^{th}$ thermal signal cycle. As used herein, time lengths refer to time intervals measured from a common key time point (e.g., corresponding to R wave peak ECG value or other synchronizing signal value), while each time duration refers to a time interval measured between time points corresponding to a particular temperature amplitude (e.g., ROI Temp2, ROI Temp1, Average base Temp, etc.). See, for example, segmented thermal signal cycle 510 in FIG. 5. As shown by the equations (8) to (13), three types of time lengths ($\Delta T$, $\Delta T1$, $\Delta T2$) and three types of time durations (T, T1, T2) of the segmented thermal signal waveform are used to estimate the time-based CO indices. It should be appreciated, however, that other different kinds of time lengths and/or durations may also be used.

Delay timing CO indices may be determined based on temperature gating parameters derived from other non-thermal patient signals (e.g., ECG, NIBP, etc.) as follows:

$$CO_{T\_delay\_0}(n) = \theta_0(t) \cdot TDL(n) \quad (14)$$

$$CO_{T\_delay\_1}(n) = \theta_1(t) \cdot \frac{TDL(n)}{\Delta T(n)} \quad (15)$$

$$CO_{T\_delay\_2}(n) = \theta_2(t) \cdot Var(TDL(n))|_M \quad (16)$$

wherein $CO_{T\_delay\_x}$ (n) is the delay timing CO index; TDL(n) is the gating time delay between the ECG R wave peak time (or other patient signal peak time) and peak time of the thermal signal waveform for the nth cycle; $Var(TDL(n))|_M$ is the variation value of TDL(n); M is the averaging time window size for delay variation calculation; and $\theta_x(t)$ is the calculation coefficient or ratio between the temperature gating parameter value and delay timing CO index. $\theta_x(t)$ is usually dynamic for different patients and can be adaptively updated by the coefficient estimation module. For a specific patient and stable situation, $\theta_x(t)$ is usually stable and is treated as a constant factor.

A variation CO index may be determined based on the ROI temperature range variation (or thermal variation) as follows:

$$CO_{T\_ROI}(n) = \kappa(t) \cdot \left| \frac{ROITemp1(n) - ROITemp2(n)}{\Delta T1(n) - \Delta T2(n)} \right| \quad (17)$$

wherein $CO_{T\_ROI}(n)$ is the variation CO index; ROITemp1(n) and ROITemp2(n) are pre-selected ROI temperatures of the nth thermal signal cycle; $\Delta T1(n)$ and $\Delta T2(n)$ are corresponding time durations for the pre-selected ROI temperatures; and $\kappa(t)$ is a calculation coefficient or ratio between the thermal variation parameter and CO index. κ(t) is usually dynamic for different patients and can be adaptively updated by the coefficient estimation module. For a specific patient and stable situation, κ(t) is usually stable and treated as a constant factor.

The CO index may also be determined based on thermal speed or acceleration. Thermal speed or acceleration signals may be directly derived from special-purpose temperature speed/acceleration sensors and probes, which means that the CO index may also be derived directly from the sensor module. Dynamic change CO indices may be determined based on thermal speed or acceleration parameters, as follows:

$$CO_{T\_speed\_max}(n) = \psi_0 \cdot \left|\max\left(\frac{dT}{dt}\right)\right|_{T \in S(n)} \quad (18)$$

$$CO_{T\_speed\_range}(n) = \psi_1 \cdot \left|\max\left(\frac{dT}{dt}\right) - \min\left(\frac{dT}{dt}\right)\right|_{T \in S(n)} \quad (19)$$

$$CO_{T\_acceleration\_max}(n) = \psi_2 \cdot \left|\max\left(\frac{d^2T}{d^2t}\right)\right|_{T \in S(n)} \quad (20)$$

$$CO_{T\_acceleration\_range}(n) = \psi_3 \cdot \left|\max\left(\frac{d^2T}{d^2t}\right) - \min\left(\frac{d^2T}{d^2t}\right)\right|_{T \in S(n)} \quad (21)$$

wherein $CO_{T\_speed\_max}(n)$, $CO_{T\_speed\_range}(n)$, $CO_{T\_acceleration\_max}(n)$ and $CO_{T\_acceleration\_range}(n)$ denote CO indices based on maximum thermal speed amplitude, amplitude range of thermal speed, maximum thermal acceleration amplitude and thermal amplitude range of thermal acceleration respectively;

$$\frac{dT}{dt} \text{ and } \frac{d^2T}{d^2t}$$

denote speed and acceleration signals respectively of the thermal signal waveform; max(*) and min(*) are calculation functions for maximum and minimum values of the thermal cycle S(n); T represents temperature data values in thermal cycle S(n), which is the set of all temperature data in nth cycle; $\psi_x$ is a calculation coefficient or ratio between the thermal speed or acceleration parameter and the CO index. $\psi_x$ may be dynamic for different patients and can be adaptively updated by the coefficient estimation module. For a specific patient and stable situation, $\psi_x$ is usually stable and treated as a constant factor.

At 312, patient signal monitoring unit 122 integrates different types of patient data, including parameters, ratios and/or indices generated by the present framework, to generate calculation coefficients (e.g., $\alpha_1(t)$, $\alpha_2(t)$, $\beta(t)$, $\lambda(t)$, $\gamma_x(t)$, $\omega_x(t)$, $\theta_x(t)$, $\kappa(t)$, $\psi_x$, etc.). Such calculation coefficients may be used to determine CO indices in further iterations. The integration of the different types of patient data may be performed linearly or non-linearly (e.g., by artificial neural network or a fuzzy algorithm). The precision of CO index determination may be increased as more data is derived and employed in a closed-loop adaptive control, in which calculation coefficients are adjusted according to the clinical patient situation and health events.

Figure 6:
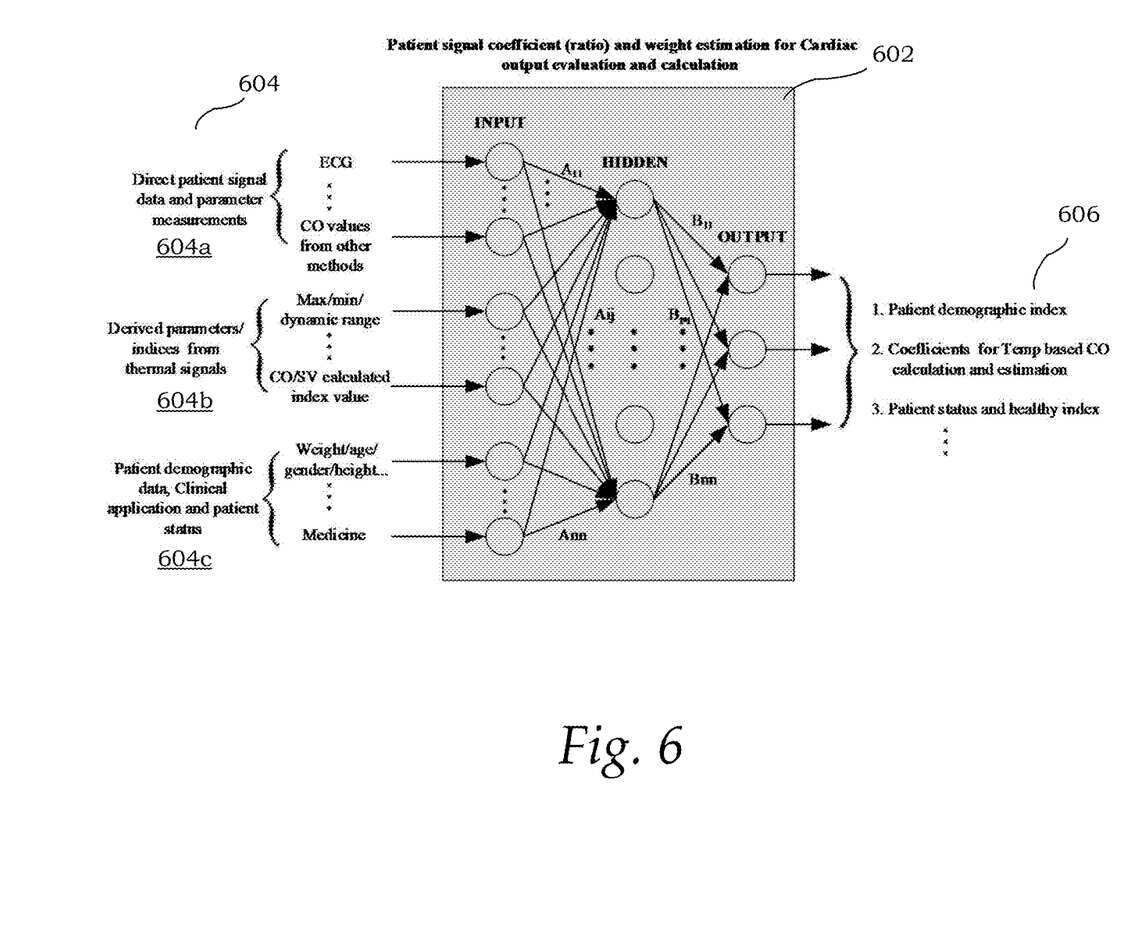
FIG. 6 shows an exemplary artificial neural network (ANN) module for multi-data fusion.

FIG. 6 shows an exemplary artificial neural network (ANN) module 602 for multi-data fusion. There are 3 layers in the ANN module 602: input layer, hidden layer and output layer. $A_{ij}$ denote weights between the input layer and the hidden layer, while $B_{pq}$ denote weights between the hidden layer and the output layer. The weights $A_{ij}$ and $B_{pq}$ can be adaptively adjusted with training data set.

The ANN module 602 has self-learning capability with new input data 604, which can increase the accuracy of calculated results 606. The ANN module 602 combines direct patient signal data and parameter measurements 604a (e.g., ECG, NIBP, CO values from other methods, etc.), parameters, indices or ratios 604b derived by the present framework (e.g., maximum/minimum/dynamic range parameters, CO indices, etc.), and patient data, clinical application and patient status 604c to generate output results 606 for detecting and treating emerging pathological events and arrhythmia. The output results 606 may include patient demographic indices, calculation coefficients for subsequent temperature-based CO index determination, patient status and health index, and so forth.

Returning to FIG. 3, at 314, patient signal monitoring unit 122 determines if further patient signal analysis is to be performed. If yes, the method 300 returns to step 304 to generate additional one or more CO indices using the calculation coefficients. If no, the method 300 proceeds to next step 316.

At 316, patient signal monitoring unit 122 evaluates the final cardiac output based on the determined CO indices. The final CO index may be derived by linearly or nonlinearly combining multiple types of CO indices. Although each index, ratio and/or defined parameter generated by the present framework may be independently utilized to evaluate cardiac output, accuracy and reliability may be improved by combining different CO indices, parameters and/or ratios. A linear or non-linear combination method may be used.

A linear combination of CO indices may be determined as follows:

$$CO/SV(n) = \delta(t) \cdot \sum_{i \in N} \tau_i \cdot CO_i(n) \quad (22)$$

wherein CO/SV(n) is the combinational cardiac output and stroke volume index; $CO_i(n)$ denotes multiple CO indices determined from the nth thermal signal cycle by using the present framework; $\tau_i$ is the integration ratio that determines the contribution of each CO calculation index ($\tau_i$ may be linear and fixed, or adaptively adjusted); $\delta(t)$ is the ratio between the real cardiac output and the CO index, which may depend on the patient size, gender, weight and location of the temperature sensors. In some clinical applications, the integration ratio $\tau_i$ and $\delta(t)$ ratio may be affected by the procedure or medicine delivery, such as hyperthermia, blood injection, environment air flow, etc.

In addition to the linear or non-linear combination of different kinds of CO indices, different types of statistical analysis may also be performed using the thermal signal waveform and associated parameters (e.g., temperature energy variability, temperature waveform entropy, etc.), which may further be linked to the cardiac output of the heart.

At 318, patient signal monitoring unit 122 may optionally adaptively adjust calculation parameters used for calculating the aforementioned parameters, ratios and/or indices. The adaptive adjustment may be performed automatically, semi-automatically or manually by the clinical user based on clinical experience and knowledge. Such calculation parameters may include, but are not limited to, coefficients, calculation window size, signal portion, ROI area, time steps, severity thresholds, and so forth. Such calculation parameters may be re-input into the ANN module 602 so as to improve stability and sensitivity (true positive and false positive rate) of the output results.

At 320, patient signal monitoring unit 122 generates a patient report. The patient report may present any cardiac abnormality, associated characteristics (e.g., location, type, severity, timing, etc.) and other information (e.g., suggested treatment options). The patient report may be in the form of, for example, an alert message, warning or indicator. The patient report may also be stored in database 124 for future retrieval, transmitted or shared with other client computers, and/or printed in physical form for viewing.

The CO indices derived from the thermal signal data can be used in many clinical applications, such as operating room clinical monitoring, ICU/CCU critical monitoring, EM (emergency room) patient status and health monitoring, etc. CO/SV is a key factor for patient monitoring, whereby any kind of deviation may help to facilitate early detection of patient abnormality and predict patient pathology and suitable treatment.

Figure 7:
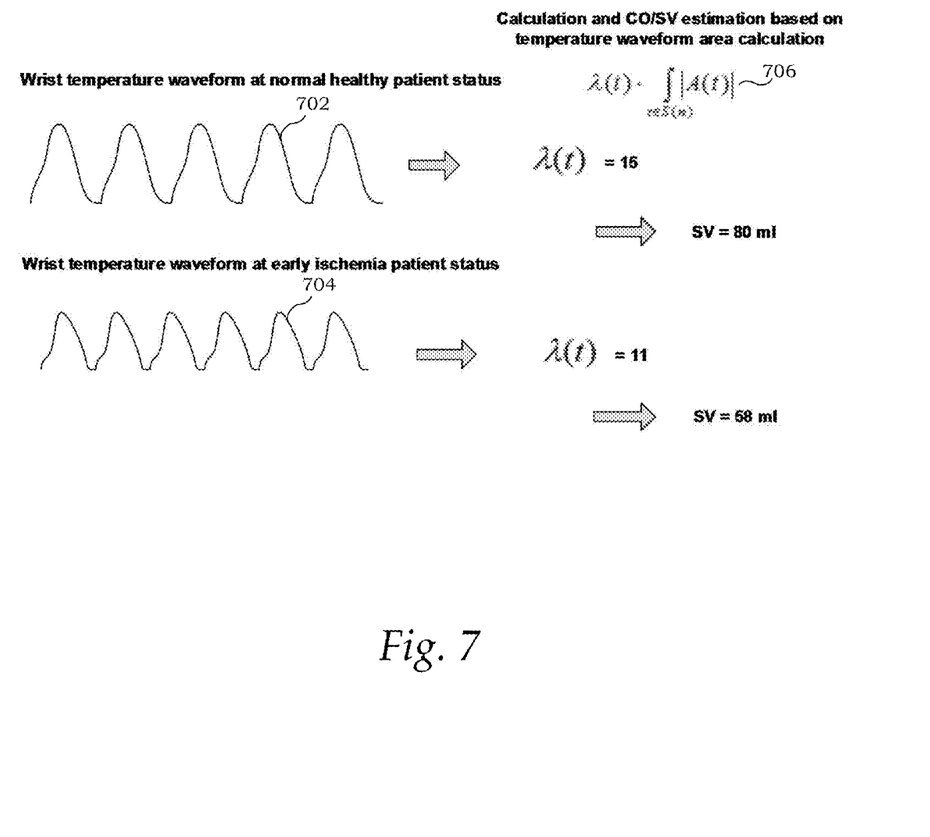
FIG. 7 illustrates two computer simulated episodes of cardiac status.

FIG. 7 illustrates two computer simulated episodes of cardiac status. More particularly, a wrist thermal signal waveform 702 for a normal healthy patient status (at rest) and a wrist thermal signal waveform 704 for an early myocardial ischemia event (during exercise) are simulated. CO values calculated by conventional X-ray image technology may be compared with the waveform area CO indices 706 determined by the present framework. In the normal healthy stage, the coefficient ($\lambda(t)$) is set to 15 while the coefficient for the early ischemia event is set to 11, which is based on the simulation data and pre-clinical knowledge of the computer simulation model.

The heart rate of the normal situation is 70 and the early ischemia heart rate is about 85. The dynamic amplitude range of the early ischemia episode is smaller than that of the normal episode. The thermal waveform area CO index (SV) is calculated for both situations: SV for the healthy status is 80 ml, while the SV for the early ischemia event is about 58 ml. The CO ratio of the two episodes may then be determined: 80×70 (5600) vs 58×85 (4930). It is clear that during the ischemia stage, the heart pumps less blood.

In the example, different kinds or locations of thermal waveform analysis may facilitate the estimation of cardiac output and health status of the patient. Additionally, the thermal coefficient can be adaptively adjusted to track the cardiac function. For example, by using the database, CO/SV value of different kinds of condition can be derived to compare to a specific patient heart output.

While the present disclosure has been described in detail with reference to exemplary embodiments, those skilled in the art will appreciate that various modifications and substitutions can be made thereto without departing from the spirit and scope of the disclosure as set forth in the appended claims. For example, elements and/or features of different exemplary embodiments may be combined with each other and/or substituted for each other within the scope of this disclosure and appended claims.

The invention claimed is:

1. A system for patient signal analysis, comprising:
one or more thermal sensors that non-invasively acquire thermal signal data from a patient; and
a computer system communicatively coupled to the one or more thermal sensors, wherein the computer system includes
a non-transitory computer-readable media that stores computer readable program code, and
a processor in communication with the non-transitory computer-readable media, the processor being operative with the computer readable program code to perform steps including
synchronizing the thermal signal data with a blood pressure signal data,
segmenting, based on occurrence of one or more points on the synchronized blood pressure signal data, the thermal signal data into a region of interest and extracting one or more parameters from the region of interest,
repeatedly determining different types of cardiac output indices based on the one or more parameters, wherein each of the different types of cardiac output indices individually characterizes cardiac output or stroke volume,
linearly combining the different types of cardiac output indices to generate a final cardiac output index by determining a product of a ratio and a weighted sum of the cardiac output indices, wherein the ratio is dependent on a location of the one or more thermal sensors, and
controlling a treatment device by one or more control parameters based at least in part on the final cardiac output index.

2. The system of claim 1 wherein the one or more thermal sensors comprise an infrared heat-sensitive sensor, a temperature-sensitive impedance sensor, a chemical action temperature-sensitive heat sensor, a semiconductor temperature-sensitive sensor, or a combination thereof.

3. The system of claim 1, wherein the processor is further operative with the computer readable program code to repeatedly determine the cardiac output indices based on different calculation coefficients.

4. The system of claim 1 wherein the treatment device comprises an intravenous device, a pacing device, an implantable cardiac defibrillator system, a hyperthermia device, or a combination thereof.

5. The system of claim 1 further comprises an electrocardiogram sensor, a blood pressure sensor or an oximetric sensor communicatively coupled to the computer system.

6. The system of claim 1 wherein the one or more thermal sensors comprise different kinds of thermal sensors configured to be removably attached to different positions on the patient.

7. A method of patient signal analysis, comprising:
acquiring, by one or more thermal sensors, patient signal data including thermal signal data;
synchronizing the thermal signal data with blood pressure signal data;
segmenting, by a processor device, based on occurrence of one or more points on the synchronized blood pressure signal data, a region of interest from the thermal signal data;
repeatedly determining, by the processor device, different types of cardiac output indices based on parameters extracted from the segmented region of interest, wherein each of the different types of cardiac output indices individually characterizes cardiac output or stroke volume;
linearly combining the different types of cardiac output indices to generate a final cardiac output index by determining a product of a ratio and a weighted sum of the cardiac output indices, wherein the ratio is dependent on a location of the one or more thermal sensors; and controlling, by the processor device, a treatment device by generating one or more control parameters based at least in part on the final cardiac output index.

8. The method of claim 7 further comprises simultaneously acquiring the thermal signal data with the blood pressure signal data.

9. The method of claim 7 further comprises simultaneously acquiring the thermal signal data and the blood pressure signal data with oximetric signal data.

10. The method of claim 7 wherein the one or more parameters extracted from the segmented region of interest comprise at least one of time duration, time length, waveform area, amplitude, amplitude range or a combination thereof.

11. The method of claim 7 wherein determining the cardiac output indices comprises determining an amplitude cardiac output index based on at least one temperature amplitude parameter.

12. The method of claim 11 wherein the at least one temperature amplitude parameter comprises a difference between a maximum amplitude and a minimum amplitude.

13. The method of claim 11 wherein the at least one temperature amplitude parameter comprises an average amplitude.

14. The method of claim 7 wherein determining the cardiac output indices comprises determining an amplitude range cardiac output index based on at least one temperature amplitude statistical parameter.

15. The method of claim 14 wherein the at least one temperature amplitude statistical parameter comprises an amplitude standard deviation.

16. The method of claim 7 wherein determining the cardiac output indices comprises determining a waveform area cardiac output index based on a temperature waveform area.

17. The method of claim 7 wherein determining the cardiac output indices comprises determining a time-based cardiac output index based on a time duration measured between time points corresponding to a particular temperature amplitude.

18. The method of claim 7 wherein determining the cardiac output indices comprises determining a delay timing cardiac output index based on a temperature gating parameter derived from another non-thermal signal data.

19. The method of claim 7 wherein determining the cardiac output indices comprises determining a variation cardiac output index based on thermal variation.

20. The method of claim 7 wherein determining the cardiac output indices comprises determining a dynamic change output index based on a thermal speed parameter.

21. The method of claim 7 wherein determining the cardiac output indices comprises determining a dynamic change output index based on a thermal acceleration parameter.

22. The method of claim 7 further comprising adaptively adjusting calculation coefficients that are used in determining the cardiac output indices based on further patient signal data.

23. The method of claim 22 wherein adaptively adjusting the calculation coefficients comprises integrating the determined cardiac output indices with the further patient signal data to generate the calculation coefficients.

24. The method of claim 7 wherein acquiring the patient signal data including the thermal signal data comprises acquiring, directly by a temperature acceleration sensor, temperature acceleration signal data and determining the cardiac output indices comprises deriving a dynamic change output index directly by calculating a difference between a maximum value and a minimum value of the temperature acceleration signal data.

25. A non-transitory computer readable medium embodying a program of instructions executable by machine to perform steps for patient signal analysis, the steps comprising:

receiving patient signal data including thermal signal data acquired by one or more thermal sensors and blood pressure signal data;

synchronizing the thermal signal data with the blood pressure signal data;

segmenting, based on occurrence of one or more points on the synchronized blood pressure signal data, a region of interest from the thermal signal data;

repeatedly determining different types of cardiac output indices based on one or more parameters extracted from the segmented region of interest, wherein each of the different types of cardiac output indices individually characterizes cardiac output or stroke volume;

linearly combining the different types of cardiac output indices to generate a final cardiac output index by determining a product of a ratio and a weighted sum of the cardiac output indices, wherein the ratio is dependent on a location of the one or more thermal sensors; and controlling a treatment device by generating one or more control parameters based at least in part on the final cardiac output index.

* * * * *